United States Patent
Ali et al.

(10) Patent No.: US 9,622,966 B2
(45) Date of Patent: Apr. 18, 2017

(54) GASTRORETENTIVE COMPOSITION ON THE BASIS OF A WATER-SOLUBLE REACTION PRODUCT FROM A VINYL GROUP-CONTAINING PRECURSOR

(75) Inventors: Shaukat Ali, Monmouth Junction, NJ (US); Carlos Santos, Piscataway, NJ (US); Anisul Quadir, Hackettstown, NJ (US)

(73) Assignee: BASF CORPORATION, Florham Park, NJ (US)

( * ) Notice: Subject to any disclaimer, the term of this patent is extended or adjusted under 35 U.S.C. 154(b) by 1049 days.

(21) Appl. No.: 12/667,793

(22) PCT Filed: Dec. 26, 2007
(Under 37 CFR 1.47)

(86) PCT No.: PCT/US2007/026347
§ 371 (c)(1),
(2), (4) Date: Mar. 15, 2011

(87) PCT Pub. No.: WO2009/008873
PCT Pub. Date: Jan. 15, 2009

(65) Prior Publication Data
US 2012/0269866 A1 Oct. 25, 2012

Related U.S. Application Data

(60) Provisional application No. 60/948,216, filed on Jul. 6, 2007.

(51) Int. Cl.
*A61K 31/192* (2006.01)
*A61K 9/00* (2006.01)
(52) U.S. Cl.
CPC .................. *A61K 9/0065* (2013.01)
(58) Field of Classification Search
CPC .................................................... A61K 9/0065
USPC .......... 424/469, 465, 468, 462, 457
See application file for complete search history.

(56) References Cited

U.S. PATENT DOCUMENTS

| | | | |
|---|---|---|---|
| 2,930,762 A * | 3/1960 | Schoenenberger | 502/159 |
| 3,634,584 A * | 1/1972 | Poole | 424/469 |
| 5,651,985 A | 7/1997 | Penners et al. | |
| 2004/0192582 A1 | 9/2004 | Burnett et al. | |
| 2004/0208931 A1 * | 10/2004 | Friend et al. | 424/471 |
| 2005/0003000 A1 * | 1/2005 | Einig et al. | 424/451 |
| 2005/0019400 A1 * | 1/2005 | Deveney | A61K 9/2072 424/468 |

FOREIGN PATENT DOCUMENTS

EP 0669129 A2 8/1995
WO WO 2006029787 A1 * 3/2006

OTHER PUBLICATIONS

Volker Buhler, "Kollicoat Grades: Functional polymers for the Pharmaceutical Industry", published Jan. 2007 by BASF Aktiengesellschaft Pharma Solutions, p. 1-229.*
Volker Buhler "Kollicoat Grades: Functional polymers for the Pharmaceutical Industry", published Jan. 2007 by BASF Aktiengesellschaft Pharma Solutions, pp. 1-229.*
BASF (2004, http://www.in-pharmatechnologist.com/Ingredients/BASF-extends-Kollicoat-IR-range).*
BASF 2004, http://www.in-pharmatechnologist.com/Ingredients/BASF-extends-Kollicoat-IR-range.*
G. Tanbourgi, BASF—2002, http://www.pharma-ingredients.basf.com/Documents/ENP/ExAct/Nr_008_2002-05_ExAct_08.pdf.*
Sigma 2013. http://www.sigmaaldrich.com/catalog/product/aldrich/341584?lang=en&region=US.*
S. K. Saxena ("Saxena", 61 st JECFA Chem. And Tech Assess., 2004, 1-3).*
Alexander Strubel, et al, Gastroretentive Drug Delivery Systems, 3 Exp. Opin. Drug Del. 217 (2006).*
English language abstract for EP 0669129 extracted from espacenet.com database, dated Apr. 5, 2010, 14 pages.
PCT International Search Report for PCT/US2007/026347, dated May 26, 2008, 3 pages.
Article: Singh et al., "Floating Drug Delivery Systems: An Approach to Oral Controlled Drug Delivery Via Gastric Retention", Journal of Controlled Release, vol. 63, No. 3, 2000, pp. 235-259.

* cited by examiner

*Primary Examiner* — Sean Basquill
(74) *Attorney, Agent, or Firm* — Howard & Howard Attorneys PLLC (57) ABSTRACT

A gastroretentive composition comprises a mixture comprising an active ingredient component and an excipient component. The excipient component comprises a first water-soluble reaction product produced from a precursor comprising a vinyl group, and a copolymer of a polyalkylene glycol and a second water-soluble reaction product produced from a precursor comprising a vinyl group. A method of forming the gastroretentive composition comprises the steps of providing the active ingredient component and the excipient component, and mixing the active ingredient component and the excipient component to form a mixture. The mixture is aggregated to form an aggregation that is dry granulated to form a plurality of granules. The plurality of granules is processed to form the gastroretentive composition.

25 Claims, 8 Drawing Sheets

GASTRORETENTIVE COMPOSITION ON THE BASIS OF A WATER-SOLUBLE REACTION PRODUCT FROM A VINYL GROUP-CONTAINING PRECURSOR

RELATED APPLICATIONS

This patent application claims priority to and all advantages of International Patent Application No. PCT/US2007/026347, filed on Dec. 26, 2007, which claims priority to U.S. Provisional Patent Application No. 60/948,216, which was filed on Jul. 6, 2007.

BACKGROUND OF THE INVENTION

1. Field of the Invention

The subject invention generally relates to a gastroretentive composition. More specifically, the subject invention relates to a gastroretentive composition that includes an excipient component and an active ingredient component. The gastroretentive composition is used as a floating drug delivery system (FDDS).

2. Description of the Related Art

Medicinal compositions are typically administered in doses to a body to cure, minimize, and/or prevent symptoms of illness and/or injury. A medicinal composition may be administered in many different ways. For example, a medicinal composition may be administered orally as a liquid or tablet to absorb through a stomach, by inhalation as a vapor into a lung, or by injection as a liquid into a vein or a muscle. Oral administration of medicinal compositions is most typical due to ease of administration and increased likelihood of patient compliance.

Medicinal compositions may be useful for immediate or extended- and/or sustained-release in the body. Immediate-release compositions deliver a complete dose upon administration. In contrast, extended- and/or sustained-release compositions enable prolonged and continuous input of the dose to the body. Extended- and/or sustained-release compositions may be further classified according to function. For example, a gastroretentive composition is an extended- and/or sustained-release composition that remains in the stomach for an extended residence time to allow spatial- and time-controlled dose delivery. Gastroretentive compositions are typically selected for applications which require improved solubility in a low pH environment such as the stomach.

Gastroretentive compositions may be used as floating drug delivery systems where the gastroretentive composition floats aloft gastric fluids in the stomach. Floating drug delivery systems are less likely to be expelled from the stomach prematurely as compared to other extended- and/or sustained-release compositions since solids are typically expelled from the stomach before gastric fluids.

Gastroretentive compositions may be produced by wet granulation or dry granulation, and typically comprise an active ingredient and at least one excipient, such as a binder, a coating, a filler, or a lubricant. Wet granulation is conducted by adding a liquid binder to the active ingredient to produce a wet granulate, screening the wet granulate into pellets, drying and adding a dry lubricant to the pellets, and compressing the pellets in a die to form tablets. In contrast, dry granulation is conducted on a press or a roller compactor using only dry active ingredients and excipients. Dry granulation is useful for active ingredients that are sensitive to moisture, and is typically selected for applications that require shorter processing times, streamlined equipment, and decreased equipment and raw material costs.

Many existing gastroretentive compositions include excipients comprising gas-generating ingredients such as inorganic bases and organic acids. Such gas-generating ingredients react with ambient moisture and contribute to instability and premature dissolution of the gastroretentive compositions during storage.

Additionally, many existing gastroretentive compositions have higher bulk densities than gastric fluids. Higher bulk densities prevent flotation aloft gastric fluids. Without flotation aloft gastric fluids, the gastroretentive compositions are prematurely expelled from the stomach without adequate residence time for absorption into the body.

Further, many existing gastroretentive compositions are prone to moisture absorption. Moisture absorption may decrease an effectiveness of active ingredients, alter a chemical composition of active ingredients, and/or contribute to instability and premature dissolution of gastroretentive compositions during storage and/or administration.

Finally, many existing gastroretentive compositions exhibit low binding properties. Low binding properties require gastroretentive compositions to be produced by wet granulation, which increases processing times and equipment and raw material costs as compared to dry granulation.

Due to the inadequacies of the existing gastroretentive compositions, there remains an opportunity to provide a gastroretentive composition which improves upon existing gastroretentive compositions.

SUMMARY OF THE INVENTION AND ADVANTAGES

The subject invention provides a gastroretentive composition comprising a mixture comprising an active ingredient component and an excipient component. The excipient component comprises a first water-soluble reaction product produced from a precursor comprising a vinyl group, and a copolymer of a polyalkylene glycol and a second water-soluble reaction product produced from a precursor comprising a vinyl group. The first water-soluble reaction product and the second water-soluble reaction product may be the same or different.

The subject invention also provides a method of forming the gastroretentive composition. For the method, the active ingredient component and the excipient component are each provided. The active ingredient component and the excipient component are mixed to form a mixture. The mixture is aggregated to form an aggregation, and the aggregation is dry granulated to form a plurality of granules that are processed to form the gastroretentive composition.

The excipient component of the gastroretentive composition exhibits excellent binding properties, which enables the gastroretentive composition to be produced by dry granulation to minimize processing times and equipment and raw material costs. The gastroretentive composition also exhibits improved hardness which decreases friability, prevents excessive dusting, and enables efficient processing of the gastroretentive composition.

The excipient component of the gastroretentive composition is typically substantially free from gas-generating ingredients such as inorganic bases and organic acids. Therefore, the gastroretentive composition exhibits excellent resistance to moisture absorption and is typically stable during storage.

The excipient component of the gastroretentive composition exhibits excellent water solubility which enables efficient dissolution and absorption of the gastroretentive composition in the stomach. The gastroretentive composition typically has a lower bulk density than gastric fluids and therefore typically floats aloft gastric fluids in the stomach. Therefore, the gastroretentive composition typically has extended- and/or sustained release, i.e., adequate residence time in the stomach for absorption, and is not prematurely expelled from the stomach without absorption.

BRIEF DESCRIPTION OF THE DRAWINGS

Other advantages of the present invention will be readily appreciated, as the present invention becomes better understood by reference to the following detailed description when considered in connection with the accompanying drawings wherein.

DETAILED DESCRIPTION OF THE INVENTION

Figure 1:
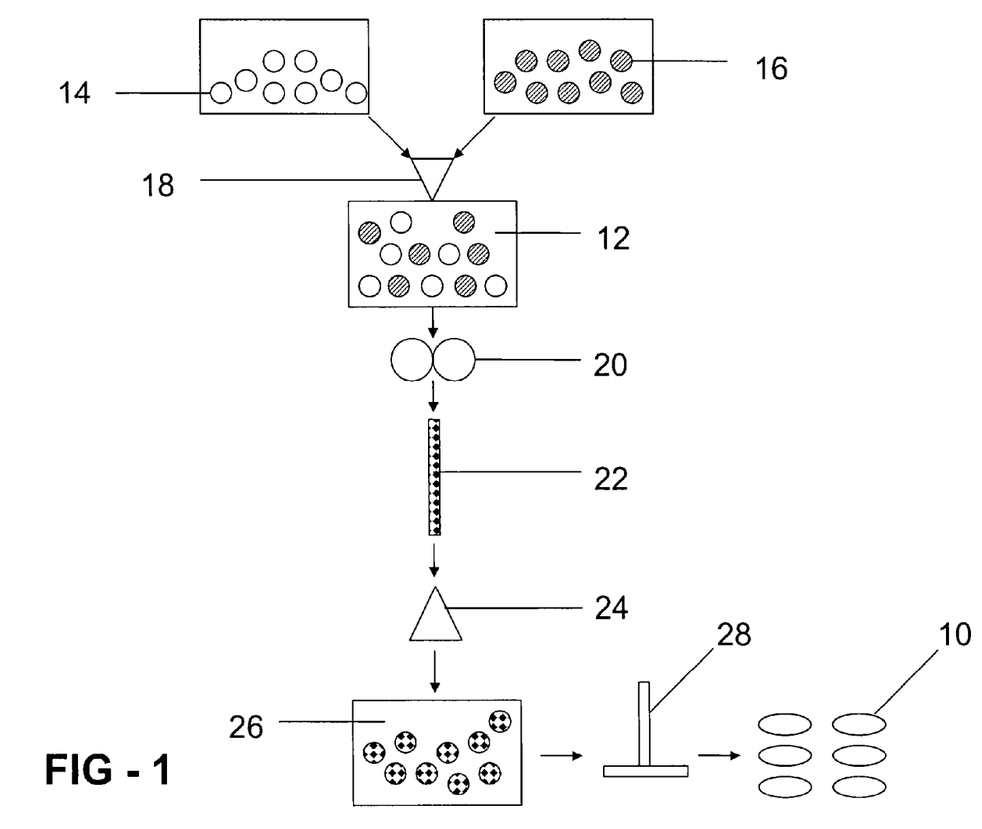
FIG. 1 is a flowchart generally illustrating a method of forming a gastroretentive composition.

A gastroretentive composition 10 and a method of forming the gastroretentive composition 10 are generally set forth in FIG. 1. The gastroretentive composition 10 may be used as a floating drug delivery system (FDDS) where the gastroretentive composition 10 floats aloft gastric fluids in a stomach. However, it is to be appreciated that the gastroretentive composition 10 and method of the present invention can have applications beyond floating drug delivery systems, such as in bioadhesive drug delivery systems.

The gastroretentive composition 10 of the present invention comprises a mixture 12 comprising an active ingredient component 14 and an excipient component 16. The active ingredient component 14 is typically useful for curing, minimizing, and/or preventing symptoms of illness and/or injury. As such, the active ingredient component 14 may be any active ingredient component known in the art. One skilled in the art may select the active ingredient component 14 based on a symptom to be cured, minimized, or prevented. Suitable active ingredient components include, but are not limited to antacids, reflux suppressants, antiflatulents, antidopaminergics, proton pump inhibitors, hydrogen receptor antagonists, cytoprotectants, prostaglandin analogues, laxatives, antispasmodics, antidiarrhoeals, bile acid sequestrants, opioids, beta-receptor blockers, calcium channel blockers, diuretics, cardiac glycosides, antiarrhythmics, nitrates, antianginals, vasoconstrictors, vasodilators, peripheral activators, angiotensin-converting enzyme (ACE) inhibitors, angiotensin receptor blockers, alpha blockers, anticoagulants, heparins, antiplatelets, fibrinolytics, antihemophilics, haemostatics, hypolipidaemic agents, statins, antipsychotics, antidepressants, anti-emetics, anticonvulsants, antiepileptics, stimulants, muscle relaxants, neuromusculars, anticholinesterase, anti-fungals, analgesics, antibiotics, antihistamines, steroids, hormones, contraceptives, supplements, vitamins, and anti-inflammatories such as non-steroidal anti-inflammatory drugs (NSAIDs). The active ingredient component 14 may be water-soluble or poorly-soluble. It is to be appreciated that the terms water-soluble and poorly-soluble refer to an ability or an inability, respectively, of the active ingredient component to dissolve in water at standard temperature and pressure. In one embodiment, the active ingredient component 14 is an analgesic. A specific example of an active ingredient component 14 is ibuprofen, commercially available from BASF Corporation of Florham Park, N.J.

The active ingredient component 14 is typically dispersed with the excipient component 16 in the mixture 12, as set forth in more detail below. That is, the active ingredient component 14 may be distributed substantially uniformly throughout the mixture 12. It is to be appreciated that the term substantially uniformly means that any first sample and any second sample of the mixture 12 will comprise an about equal amount of the active ingredient component 14 and therefore an about equal amount of the excipient component 16. In one embodiment, the excipient component 20 does not encapsulate the active ingredient component 10. That is, the excipient component 20 is not a coating. The active ingredient component 14 is typically in powder form, i.e., in a form of fine particles that are substantially free of moisture and not cemented together. It is to be appreciated that the term substantially free of moisture means that the active ingredient component 14 includes less than 0.50 parts by weight of moisture based on 100 parts by weight of the active ingredient component 14. The active ingredient component 14 typically has a particle size of from 25 to about 1,000 μm.

The active ingredient component 14 is typically present in the gastroretentive composition 10 as a salt or in free form in an amount of from about 5 to about 85, more typically from about 5 to 50 parts by weight based on 100 parts by weight of the gastroretentive composition 10. One skilled in the art typically selects the amount of the active ingredient component 14 present in the gastroretentive composition 10 based on an intensity of the symptom to be cured, minimized, or prevented by the gastroretentive composition 10.

The excipient component 16 is typically useful as a carrier for the active ingredient component 14 and for augmentation of the gastroretentive composition 10. Such augmentation of the gastroretentive composition 10 may include, but is not limited to, binding, filling, and/or lubricating the gastroretentive composition 10.

The excipient component 16 is also typically in powder form, i.e., in a form of fine particles that are substantially free of moisture and not cemented together. It is to be appreciated that the term substantially free of moisture means that the excipient component 16 includes less than 0.50 parts by weight of moisture based on 100 parts by weight of the excipient component 16. The excipient component 16 typically has a particle size of from 100 to about 1,000 μm.

The excipient component 16 typically comprises a first water-soluble reaction product produced from a precursor comprising a vinyl group and a copolymer of a polyalkylene and a second water-soluble reaction product produced from a precursor comprising a vinyl group. The first water-soluble reaction group and the second water-soluble reaction group may be the same or different. For example, the first water-soluble reaction product and the second water-soluble reaction product may each be polyvinyl alcohol. Or, only the first water-soluble reaction product may be polyvinyl alcohol. Similarly, only the second water-soluble reaction product may be polyvinyl alcohol. Typically, the first water-soluble reaction product and the second water-soluble reaction product are both polyvinyl alcohol. It is to be appreciated that the term water-soluble refers to an ability of the first water-soluble reaction product and the second water-soluble reaction product to each dissolve in water at standard temperature and pressure. A concentration of the first water-soluble reaction product is typically about 40 g of the first water-soluble reaction product per 100 ml of water. A concentration of the second water-soluble reaction product is typically about 45 g of the second water-soluble reaction product per 100 ml of water.

The excipient component 16 may comprise polyvinyl alcohol and a copolymer of polyvinyl alcohol and a polypropylene glycol. Typically, the excipient component 16 comprises polyvinyl alcohol and a copolymer of polyvinyl alcohol and polyethylene glycol, i.e., a polyvinyl alcohol-polyethylene glycol copolymer (PVA-PEG copolymer).

Without intending to be limited by theory, it is believed that the polyvinyl alcohol provides the gastroretentive composition 10 comprising the excipient component 16 with hardness. An increased hardness decreases friability, i.e., decreases a likelihood of crumbling, prevents excessive dusting, and enables efficient processing of the gastroretentive composition 10. The polyvinyl alcohol typically also provides the gastroretentive composition 10 comprising the excipient component 16 with resistance to moisture absorption and excellent binding properties as discussed in more detail below. The first water-soluble reaction product and the second water-soluble reaction product typically each independently have a weight average molecular weight of from about 30,000 to about 200,000 Daltons. It is to be appreciated that the polyvinyl alcohol typically has a dynamic viscosity that varies according to the weight average molecular weight. That is, a low-grade polyvinyl alcohol has a comparatively low viscosity of from about 4 to about 7 mPa·s at 20° C. and a weight average molecular weight of less than or equal to about 30,000 Daltons. A medium-grade polyvinyl alcohol typically has a comparatively medium viscosity of from about 21 to about 33 mPa·s at 20° C. and a weight average molecular weight of from about 30,000 to about 130,000 Daltons. A high-grade polyvinyl alcohol has a comparatively high viscosity of from about 40 to about 65 mPa·s at 20° C. and a weight average molecular weight of from about 130,000 to about 200,000 Daltons.

Examples of suitable polyvinyl alcohols for the purposes of the present invention typically have the general structure:

where n is from about 500 to about 5,000. The polyvinyl alcohol is typically the first water-soluble reaction product and the second water-soluble reaction product produced from the precursor comprising a vinyl group. More specifically, the polyvinyl alcohol is typically produced by hydrolysis of polyvinyl acetate. Polyvinyl acetate is typically produced by polymerization of the precursor comprising a vinyl group, i.e., vinyl acetate. A suitable polyvinyl alcohol is commercially available under the trade name Celvol® from Celanese of Calvert City, Ky. The polyvinyl alcohol is typically present in the excipient component 16 in an amount of from about 30 to about 85 parts by weight based on 100 parts by weight of the excipient component 16.

The polyvinyl alcohol of the PVA-PEG copolymer may be any suitable polyvinyl alcohol set forth above. The polyvinyl alcohol of the PVA-PEG copolymer may be the same or different from the polyvinyl alcohol of the excipient component 16. Typically, the polyvinyl alcohol has a weight average molecular weight of about 30,000 Daltons. The polyvinyl alcohol, i.e., the second water-soluble reaction product, is typically present in the PVA-PEG copolymer in an amount of from about 20 to about 80 parts by weight based on 100 parts by weight of the PVA-PEG copolymer.

Typically, the copolymer is a graft copolymer. That is, the copolymer typically comprises side polymer chains and main polymer chains formed by a reaction product of the polyvinyl alcohol and the polyethylene glycol (a PVA-PEG graft copolymer). The graft copolymer typically has a weight ratio of second water-soluble reaction product to polyalkylene glycol of about 1:3 to about 3:1. More specifically, the PVA-PEG graft copolymer typically has a weight ratio of polyvinyl alcohol to polyethylene glycol of about 1:3 to about 3:1. The PVA-PEG graft copolymer typically has a weight average molecular weight of from about 40,000 to about 50,000 Daltons.

Without intending to be limited by theory, it is believed that the polyethylene glycol provides the excipient component 16 with water solubility. An excellent water solubility enables efficient dissolution and absorption of the gastroretentive composition 10 in the stomach. The polyethylene glycol typically has a weight average molecular weight of from about 200 to about 12,000. Examples of suitable polyethylene glycols for the purposes of the present invention typically have the general structure:

where n is from 22.3 to 32.5. The polyethylene glycol is typically produced by polymerization of ethylene oxide. A suitable polyethylene glycol is commercially available under the trade name Lutrol® E from BASF Corporation of Florham Park, N.J.

The polyethylene glycol is typically present in the PVA-PEG copolymer in an amount of from 5 to 30, more typically 20 to 28 parts by weight based on 100 parts by weight of the PVA-PEG copolymer. More specifically, the PVA-PEG copolymer typically has a weight ratio of polyvinyl alcohol to polyethylene glycol of about 1:3 to about 3:1.

Examples of suitable PVA-PEG copolymers for the purposes of the present invention typically have the general structure:

A suitable PVA-PEG copolymer is commercially available under the trade name Kollicoat® IR from BASF Corporation of Florham Park, N.J. The PVA-PEG copolymer is typically present in the excipient component 16 in an amount of from about 20 to about 80 parts by weight based on 100 parts by weight of the excipient component 16.

The excipient component 16 of the present invention is typically substantially free from gas-generating ingredients such as inorganic bases and organic acids. By the term substantially free from gas-generating ingredients, it is meant that the excipient component 16 typically has, on average, less than 0.01 parts by weight of inorganic bases and organic acids based on 100 parts by weight of the excipient component 16. As such, the gastroretentive composition 10 is typically stable during storage since gas-generating ingredients may react with ambient moisture to create carbon dioxide and contribute to instability and premature dissolution of the gastroretentive composition 10 during storage.

Since the excipient component 16 typically comprises the polyvinyl alcohol in addition to the polyvinyl alcohol of the PVA-PEG copolymer, the excipient component 16 is also typically resistant to moisture absorption and exhibits excellent binding properties that enable the gastroretentive composition 10 to be produced by dry granulation, as set forth in more detail below. Without intending to be limited by theory, it is believed that the polyvinyl alcohol provides resistance to moisture absorption and excellent binding properties by protecting against hydrolysis reactions. Since moisture absorption may decrease an effectiveness of the active ingredient component 14, alter a chemical composition of the active ingredient component 14, and/or contribute to instability and premature dissolution of the gastroretentive composition 10 during storage and/or administration, the gastroretentive composition 10 of the present invention minimizes the aforementioned inadequacies.

Examples of suitable excipient components for the purposes of the present invention typically have the general structure:

A suitable example of the excipient component 16 for the purposes of the present invention is Kollicoat® Protect, commercially available from BASF Corporation of Florham Park, N.J.

The excipient component 16 is typically present in the gastroretentive composition 10 in an amount of from 15 to about 95 parts by weight based on 100 parts by weight of the gastroretentive composition 10. One skilled in the art typically selects the amount of the excipient component 16 present in the gastroretentive composition 10 based on the amount of the active ingredient component 14 in the gastroretentive composition 10 and desired properties, such as flotation, hardness, and/or moisture absorption of the gastroretentive composition 10.

The gastroretentive composition 10 may further comprise a coating agent that is typically a polymer. Suitable coating agents may be any coating agent known in the art. The coating agent is typically useful for protecting the gastroretentive composition 10 and for reducing a lag time, $t_{lag}$, i.e., a time before the gastroretentive composition 10 floats after contacting gastric fluids, of the gastroretentive composition 10. It is to be appreciated that the coating agent, if present, is typically different from the excipient component 16. That is, the excipient component 16 is typically dispersed with the active ingredient component 14 in the mixture 12, whereas the coating agent typically coats the gastroretentive composition 10 to protect the gastroretentive composition 10 and reduce the lag time, $t_{lag}$. Examples of suitable coating agents include, but are not limited to, synthetic polymers, shellac, and cellulose.

The gastroretentive composition 10 may further comprise a granulating agent. Suitable granulating agents may be any granulating agent known in the art. The granulating agent is typically useful for agglomerating the excipient component 16 and the active ingredient component 14 and for reducing the lag time, $t_{lag}$, of the gastroretentive composition 10. Typically, the granulating agent is a polymer. The granulating agent is typically selected from the group of a polyvinyl pyrrolidone, polyvinyl acetate, polyvinyl alcohol, polyoxy propylene-polyoxy ethylene copolymer, a polyacrylic acid-based polymer, and combinations thereof.

The gastroretentive composition 10 may further comprise an additive component. If included, the additive component is selected from the group of an antiadherent, a colorant, a lubricant, a filler, a binder, a flavorant, a glidant, a preservative, a solubilizer, a disintegrant, and combinations thereof.

Suitable antiadherents may be any antiadherent known in the art. The antiadherent is typically useful for reducing adhesion between the gastroretentive composition 10 and processing equipment and/or packaging. Examples of suitable antiadherents include, but are not limited to, magnesium stearate and talc.

Suitable colorants may be any colorant known in the art. The colorant is typically useful for improving an appearance of the gastroretentive composition 10 and for increasing patient compliance by allowing for efficient identification of the gastroretentive composition 10. Examples of suitable colorants include, but are not limited to, water-soluble iron oxides, dyes, lakes, and pigments such as talc, titanium dioxide, and kaolin.

Suitable lubricants may be any lubricant known in the art. The lubricant is useful for preventing the active ingredient component 14 from clumping and for ensuring efficient processing. Examples of suitable lubricants include, but are not limited to, talc, silica, fats, magnesium stearate, and stearic acid.

Suitable fillers may be any filler known in the art. The filler is typically useful for increasing a volume of the gastroretentive composition 10 to ensure efficient processing and allow for convenient size for administration. Examples of suitable fillers include, but are not limited to, cellulose, dibasic calcium phosphate, lactose, sucrose, glucose, mannitol, sorbitol, calcium silicate, and calcium carbonate.

Suitable binders may be any binder known in the art. The binder is typically useful for congealing the gastroretentive composition 10 and ensuring the gastroretentive composition 10 can be produced with required mechanical strength. Examples of suitable binders include, but are not limited to, starches, sugars, cellulose, and sugar alcohols such as xylitol, sorbitol, or maltitol.

Suitable flavorants may be any flavorant known in the art. The flavorant is typically useful for improving a taste of the gastroretentive composition 10. Examples of suitable flavorants include, but are not limited to, essential oils, oleoresin, essence, extractive, protein hydrolysate, distillate, and any product of roasting, heating, and enzymolysis, which derives from a spice, fruit, vegetable, edible yeast, herb, bark, bud, root, leaf, and any edible portions of plants, meats seafood, poultry, eggs, dairy products, and fermentation products thereof.

Suitable glidants may be any glidant known in the art. The glidant is typically useful for improving a flowability of the excipient component 16 and/or the active ingredient component 14 and for reducing adhesion between the gastroretentive composition 10 and processing equipment and/or packaging. Examples of suitable glidants include, but are not limited to, colloidal silica, silica gel, precipitated silica, and talc.

Suitable preservatives include any known preservative in the art. The preservative is typically useful for preventing spoilage of the active ingredient component 14 caused by microbial growth or chemical changes. Examples of suitable preservatives include, but are not limited to, amino acids, citric acid, sodium citrate, methyl paraben, propyl paraben, and antioxidants such as vitamin A, vitamin C, and vitamin E.

Suitable solubilizers include any known solubilizer in the art. The solubilizer is typically useful for increasing solubility of the excipient component 16 and the active ingredient component 14 and for reducing the lag time, $t_{lag}$, of the gastroretentive composition 10. Typically, the solubilizer has a hydrophilic-lipophilic balance (HLB) range of from about 5 to about 30. Suitable examples of solubilizers include, but are not limited to, Lutrol® grades, Cremophor® EL, Cremophor® RH 40, and Solutol® HS 15, commercially available from BASF Corporation of Florham Park, N.J. Other suitable examples of solubilizers include, but are not limited to, Tween® 80, commercially available from Uniqema of Chicago, Ill., and vitamin E-TPGS, commercially available from Eastman Chemical Company of Kingsport, Tenn.

Suitable disintegrants include any known disintegrant in the art. The disintegrant is typically useful for encouraging the gastroretentive composition 10 to break apart in the stomach to promote absorption of the active ingredient component 14. Examples of suitable disintegrants include, but are not limited to, starch, cellulose, crosslinked polyvinyl pyrrolidone, sodium starch glycolate, and sodium carboxymethyl cellulose.

In one embodiment, the gastroretentive composition 10 comprises the mixture 12 comprising the active ingredient component 14 comprising ibuprofen and the excipient component 16 comprising polyvinyl alcohol and the graft copolymer of polyethylene glycol and polyvinyl alcohol. The active ingredient component 14 is dispersed with the excipient component 16 in the mixture 12, as set forth in more detail below.

For the method of forming the gastroretentive composition 10, generally set forth in FIG. 1, the active ingredient component 14 and the excipient component 16 comprising the first water-soluble reaction product and the copolymer of the polyalkylene glycol and the second water-soluble reaction product are each provided in powder form, i.e., in a form of fine particles that are substantially free of moisture and not cemented together as set forth above. Alternatively, the additive component and granulating agent may also be provided in powder form.

The active ingredient component 14 and the excipient component 16 are mixed 18 to form the mixture 12 in powder form. The active ingredient component 14 is typically dispersed with the excipient component 16 in the mixture 12. The active ingredient component 14 and the excipient component 16 may be mixed 18 by any mixing means known in the art. Typically, the active ingredient component 14, the excipient component 16, and the additive component may be combined in a blender suitable for mixing components in powder form for from about 1 to about 10 minutes at an ambient temperature of from about 22 to about 25° C., and powder sieved through a U.S.S. #20 mesh screen to form the mixture 12. The polyvinyl alcohol, i.e., the first water-soluble reaction product, is typically present in the mixture 12 in an amount of from about 30 to about 85 parts by weight based on 100 parts by weight of the mixture 12. The PVA-PEG copolymer is typically present in the mixture 12 in an amount of from about 20 to about 80 parts by weight based on 100 parts by weight of the mixture 12. More typically, the mixture 12 typically has a weight ratio of polyvinyl alcohol to PVA-PEG copolymer of about 5:1.

The mixture 12 is aggregated 20 to form an aggregation 22. The mixture 12 may be aggregated 20 by any means for aggregation known in the art. Typically, the mixture 12 is aggregated 20 by compressing the mixture 12 or by pressure rolling the mixture 12. For example, the mixture 12 may be compressed by a conventional tablet machine or a rotary press to form a slug. The slug typically has a diameter of from about 10 to 20 mm and a thickness of from about 5 to 15 mm. Alternatively, the mixture 12 may be pressure rolled by squeezing the mixture 12 between a plurality of rollers to form a compressed sheet. The compressed sheet typically has a width corresponding to a length of the plurality of rollers.

The aggregation 22, i.e., the slug or the compressed sheet, is dry granulated 24 to form a plurality of granules 26. The aggregation 22 may be dry granulated 24 by any means for dry granulation known in the art. For example, the slug may be dry granulated 24 by a hammer mill to form the plurality of granules 26. Alternatively, since the compressed sheet is typically weak and brittle, the compressed sheet may naturally break into flakes upon exit from the plurality of rollers. The flakes are typically screened with a mesh screen to form the plurality of granules 26. Each of the plurality of granules 26 typically has a diameter of from about 0.2 to 1.5 mm.

The plurality of granules 26 is processed 28 to form the gastroretentive composition 10. In a first embodiment, the plurality of granules 26 may be compressed to form the gastroretentive composition 10. The plurality of granules 26 are typically compressed on a Carver press or a high speed rotary press.

In the first embodiment, the resulting gastroretentive composition 10 is a tablet. The tablet may be a single-layer tablet or a multi-layer tablet. The tablet typically has a diameter of from about 5 to about 15 mm, a thickness of from about 5 to about 10 mm, and a weight of from about 5 to 900 mg, typically 400 mg. The resulting gastroretentive composition 10 typically has a hardness of from about 5 to 30 kP as measured by a HT-500 hardness tester commercially available from Key International, Inc. of Englishtown, N.J. Without intending to be limited by theory, it is believed that the polyvinyl alcohol provides the gastroretentive composition 10 with hardness. An increased hardness decreases friability, prevents excessive dusting, and enables efficient processing of the gastroretentive composition 10. The polyvinyl alcohol typically also provides the gastroretentive composition 10 with excellent binding properties. Since poor binding properties require gastroretentive compositions to be produced by wet granulation, which increases processing times and equipment and raw material costs, the gastroretentive composition 10 of the present invention may be produced by dry granulation, as set forth above. Dry granulation is useful for active ingredient components that are sensitive to moisture, and is typically selected for applications that require shorter processing times, streamlined equipment, and decreased equipment and raw material costs.

In the first embodiment, the tablet may be coated with the coating agent to improve appearance, taste, and/or ease of swallowing. The tablet may be coating by any means for coating as known in the art. For example, the tablet may be spray-coated, dip-coated, or brush-coated.

In a second embodiment, the plurality of granules 26 may be encapsulated by a capsule to form the gastroretentive composition 10. The capsule may be selected from the group of a hard-shelled capsule and a soft-shelled capsule. Typically, the capsule is the hard-shelled capsule. The capsule may comprise gelatin, a carrageenan, modified forms of starch and cellulose, and combinations thereof. The hard-shelled capsule and the soft-shelled capsule are typically clear, colorless, and tasteless, although colorants and flavorants may be added for UV protection and efficient identification of the gastroretentive composition 10.

The plurality of granules 26 may be encapsulated by the capsule by any means for encapsulation known in the art. For example, the plurality of granules 26 are typically encapsulated by the soft-shelled capsule via a rotary die in combination with blow molding. The plurality of granules 26 are typically encapsulated by the hard-shelled capsule by providing the hard-shelled capsule having two halves. Before encapsulation, the two halves are typically separated and the hard-shelled capsule may be filled with the plurality of granules 26. The two halves of the hard-shelled capsule are then typically pressed together to form the gastroretentive composition 10.

In the second embodiment, the resulting gastroretentive composition 10 is a filled capsule. That is, the active ingredient component 14 and excipient component 16 are disposed inside the capsule. The filled capsule may be generally oval and typically has a length of from about 5 to about 30 mm, a width of from about 5 to about 10 mm, and a weight of from about 5 to 1,000 mg, typically 400 mg.

In a third embodiment, the plurality of granules 26 may be sifted to form the gastroretentive composition 10. That is, the resulting gastroretentive composition 10 may be sifted with a mesh to remain in granular form. The plurality of granules 26 typically each have a particle size of about 200 to about 1,000 μm.

In a fourth embodiment, the plurality of granules 26 may be coagulated to form the gastroretentive composition 10. The plurality of granules 26 may be coagulated by any means known in the art, such as by extrusion and spheronization. In the fourth embodiment, the gastroretentive composition 10 is typically a beadlet. The beadlet typically has a diameter of from about 500 to about 3,000 μm.

The resulting gastroretentive composition 10 typically has a bulk density of from about 0.10 to about 0.30 g/ml, more typically about 0.11 g/ml. The gastroretentive composition 10 typically has a lower bulk density than gastric fluids and therefore typically floats aloft gastric fluids in the stomach. The gastroretentive composition 10 typically has a lag time, $t_{lag}$, of from about 0 to 15 minutes aloft fluid having a pH of from 1.2 to 7.2 at a temperature of about 37° C. The gastroretentive composition 10 is also typically porous, which also enables flotation aloft gastric fluids. That is, the gastroretentive composition 10 typically defines a plurality of voids. A concentration of the plurality of voids defined by the gastroretentive composition 10 may be stated as a percent porosity. The percent porosity of the gastroretentive composition 10 is typically from about 10 to about 50%.

Since the gastroretentive composition 10 typically floats aloft gastric fluids, the gastroretentive composition 10 typically has adequate residence time in the stomach for absorption and is not prematurely expelled from the stomach without absorption. The resulting gastroretentive composition 10 typically has a flotation time of from about 0 to 24 hours aloft fluid having a pH of from 1.2 to 7.2 at a temperature of about 37° C. and typically releases the active ingredient component 14 for from about 2 to 24 hours. The resulting gastroretentive composition 10 typically has a dissolution time of from about 0 to 24 hours in fluid having a pH of from 1.2 to 7.2 at a temperature of about 37° C., and is therefore typically an extended- and/or sustained-release composition. Without intending to be limited by theory, it is believed that the polyvinyl alcohol of the excipient component 16 provides the gastroretentive composition 10 with extended- and/or sustained-release due to hydration and/or swelling of the polyvinyl alcohol in the stomach.

EXAMPLES

The following examples are merely intended to illustrate the invention and are not to be viewed in any way as limiting to the scope of the invention.

Comparative Examples 1-2 and Examples 3-4

A series of excipient components, Comparative Examples 1-2 and Examples 3-4, is formed by providing 400 mg of excipient component A in powder form and 400 mg of excipient component B in powder form. Excipient component A is a polyvinyl alcohol-polyethylene glycol copolymer commercially available under the trade name Kollicoat® IR from BASF Corporation of Florham Park, N.J. Excipient component B is a physical mixture of polyvinyl alcohol and a graft copolymer of polyvinyl alcohol and polyethylene glycol commercially available under the trade name Kollicoat® Protect from BASF Corporation of Florham Park, N.J.

Excipient component A is combined with water in a blender for about 5 minutes at an ambient temperature of about 25° C. to produce a first wet granulate. The first wet granulate is screened to form a first series of pellets. The first series of pellets is dried and compressed on a Carver press to form a first series of five tablets, Comparative Example 1, comprising excipient component A. Each of the five tablets of Comparative Example 1 has a weight of 400 mg.

Likewise, excipient component B is combined with water to produce a second wet granulate. The second wet granulate is screened to form a second series of pellets. The second series of pellets is dried and compressed on a Carver press to form a second series of five tablets, Example 3, comprising excipient component B. Each of the five tablets of Example 3 has a weight of 400 mg.

Each of the excipient components of Comparative Example 1 and each of the excipient components of Example 3 are evaluated for hardness according to the ASTM E04-07 test method on a HT-500 hardness tester available from Key International of Englishtown, N.J., at compression forces of from 5 to 23 kP. Table 1 sets forth hardness values at compression forces of from 5 to 23 kP for the tablets of Comparative Example 1, comprising Kollicoat® IR, and Example 3, comprising Kollicoat® Protect. As shown in Table 1, the hardness of the tablets comprising Kollicoat® Protect is approximately 4 times higher than the hardness of the tablets comprising Kollicoat® IR at the examined compression forces.

TABLE 1

| Compression Force (kN) | Comp. Ex. 1, wet granulation Hardness (kP) | Ex. 3, wet granulation Hardness (kP) |
| --- | --- | --- |
| 5 | 5.1 | 18.9 |
| 9 | 5.5 | 21.0 |
| 14 | 6.4 | 22.1 |
| 18 | 6.0 | 23.8 |
| 23 | 5.5 | 22.7 |

Excipient component A is powder sieved through a U.S.S. #20 mesh screen to form a first sample in powder form. The first sample is compressed on a Carver press to form a first series of five tablets, Comparative Example 2, comprising excipient component A. Each of the five tablets of Comparative Example 2 has a weight of 400 mg.

Excipient component B is powder sieved through the U.S.S. #20 mesh screen to form a second sample in powder form. The second sample is compressed on the Carver press to form a second series of five tablets, Example 4, comprising excipient component B. Each of the five tablets of Example 4 has a weight of 400 mg.

Figure 2:
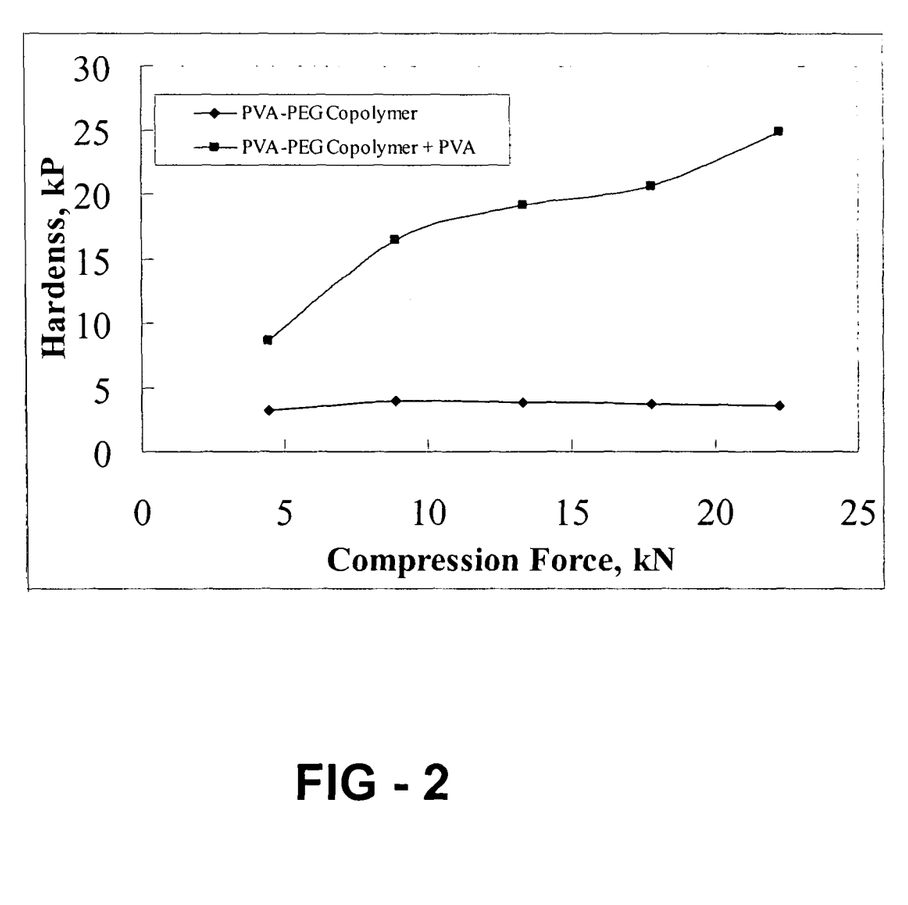
FIG. 2 is a graph illustrating hardness as a function of compression force of tablets comprising an excipient component of the present invention and of tablets comprising a conventional excipient component.

Each of the tablets of Comparative Example 2 and each of the tablets of Example 4 are evaluated for hardness according to the ASTM E04-07 test method on the hardness tester at compression forces of from 3 to 22 kP. As shown in FIG. 2, the hardness of the tablets comprising PVA-PEG Copolymer (e.g. Kollicoat® IR) is about 3-4 kP and substantially unchanged as compression force increases. In contrast, as shown in FIG. 2, the hardness of the tablets comprising PVA-PEG Copolymer+PVA (e.g. Kollicoat® Protect) increases as compression force increases. At a compression force of 22 kN, the hardness of the tablets of Example 4 comprising PVA-PEG Copolymer+PVA is about 6 times higher than the hardness of the tablets of Comparative Example 2 comprising PVA-PEG Copolymer.

Figure 3:
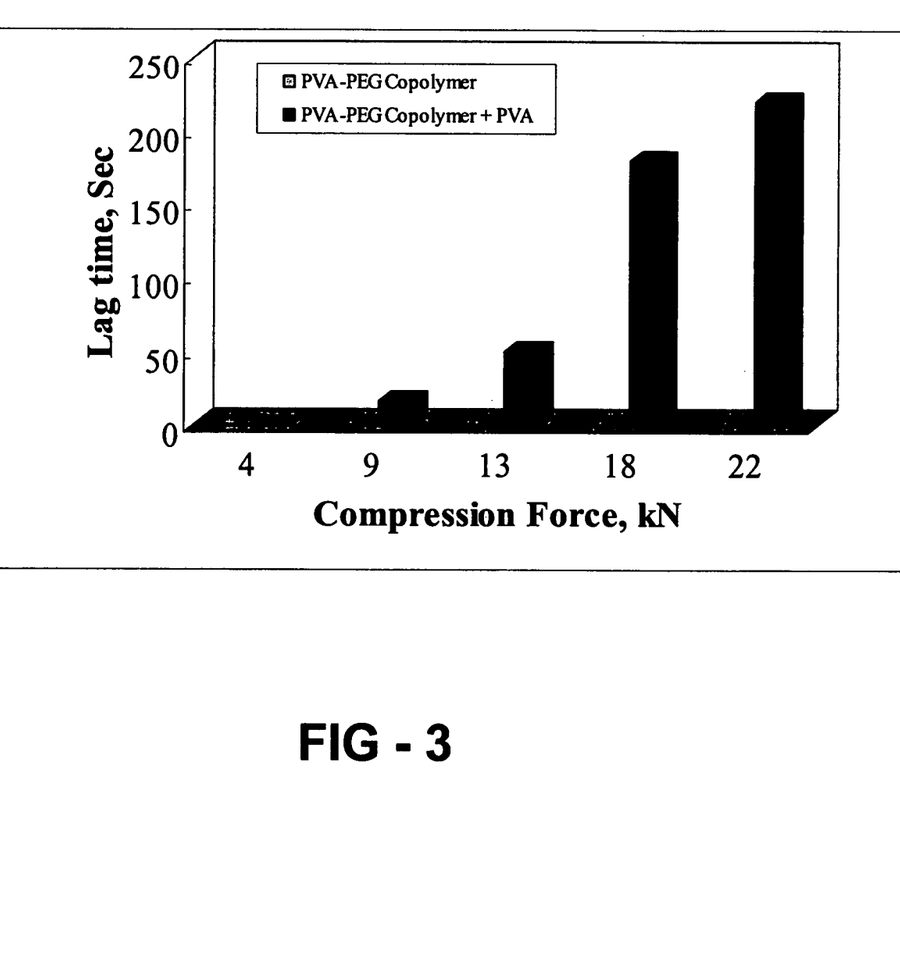
FIG. 3 is a graph illustrating lag time as a function of compression force of tablets comprising the excipient component of the present invention and of tablets comprising the conventional excipient component.

Each of the tablets of Comparative Example 2 and each of the tablets of Example 4 are evaluated for lag time in water at 25° C. As shown in FIG. 3, the tablets of Comparative Example 2 comprising PVA-PEG Copolymer float back and have a lag time of less than 1 minute and dissolve in less than 6 hours in water at 25° C. In contrast, as shown in FIG. 3, the tablets of Example 4 comprising PVA-PEG Copolymer+PVA have a lag time of 4 minutes before floating and dissolve over 24 hours in water at 25° C. Therefore, the tablets of Example 4 comprising PVA-PEG Copolymer+PVA provide improved hardness and floating characteristics for gastroretentive compositions without the use of organic acids and inorganic bases in the gastroretentive compositions. The tablets of Examples 2 and 4 comprising PVA-PEG Copolymer+PVA are useful for dosages requiring dry granulation.

Examples 5-8

A series of gastroretentive compositions, Examples 5-8, is formed by providing excipient component B in powder form and active ingredient component C in powder form according to the amounts listed in Table 1. Active ingredient component C is Ibuprofen 90 commercially available from BASF Corporation of Florham Park, N.J. Excipient component B and active ingredient component C are combined in the blender for about 5 minutes at an ambient temperature of about 25° C., and powder sieved through the U.S.S. #20 mesh screen to form a third mixture in powder form. The third mixture is compressed on the Carver press to form a third series of four tablets, Examples 5-8, comprising excipient component B and active ingredient component C. Each of the tablets of Examples 5-8 has a weight of 540 mg.

TABLE 1

| | Gastroretentive Composition | | |
| --- | --- | --- | --- |
| Ex. | PVA-PEG Copolymer + PVA (e.g. Kollicoat ® Protect), mg | Ibuprofen, mg | Ibuprofen, % |
| 5 | 270 | 270 | 50% |
| 6 | 340 | 200 | 37% |
| 7 | 405 | 135 | 25% |
| 8 | 470 | 70 | 13% |

Figure 4:
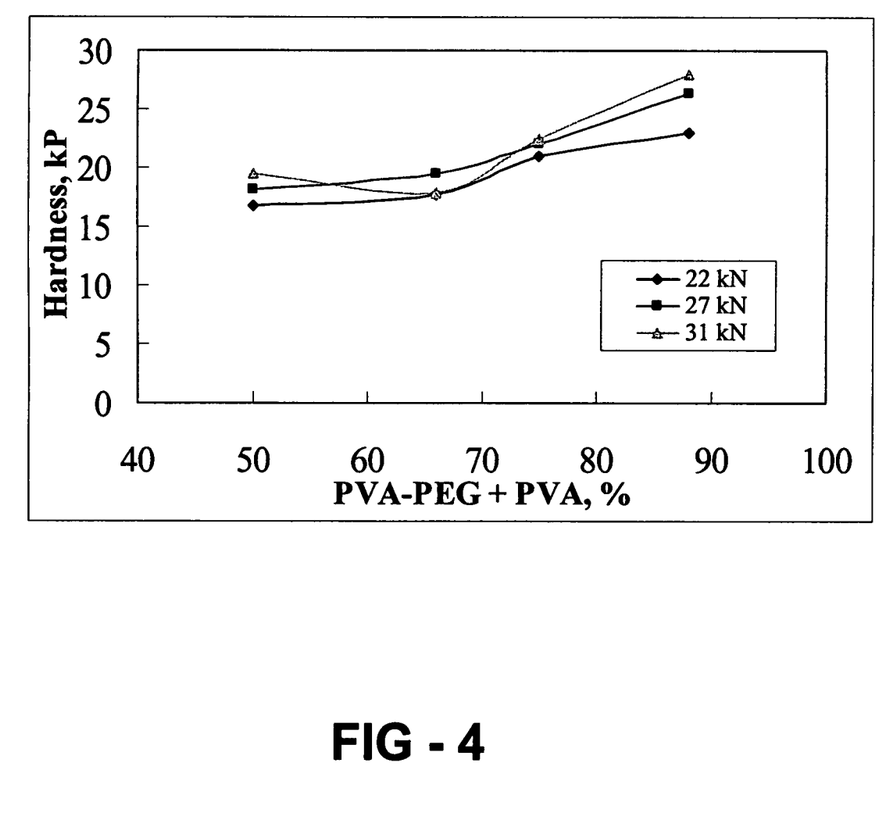
FIG. 4 is a graph illustrating hardness as a function of an amount of the excipient component of the present invention of tablets at varying compression forces.

Each of the tablets of Examples 5-8 are evaluated for hardness according to the ASTM E04-07 test method on the hardness tester at compression forces of from 22 to 31 kP. As shown in FIG. 4, the hardness of the tablets comprising PVA-PEG Copolymer+PVA increases with increased amounts of PVA-PEG Copolymer+PVA at all compression forces. Therefore, gastroretentive compositions comprising excipient component B exhibit excellent binding properties and resistance to moisture absorption and are useful for dosages requiring dry granulation.

The tablets of Examples 5-8 are evaluated for lag time aloft water, a fluid having a pH of 1.2, and a fluid having a pH of 7.2. The tablet of Example 5 does not float as readily as the tablets of Examples 6-8. That is, the tablet of Example 5 comprising 50% active ingredient component by weight has an unacceptable lag time and sluggish flotation aloft water, the fluid having a pH of 1.2, and the fluid having a pH of 7.2 as compared to the tablets of Examples 6-8.

Figure 6:
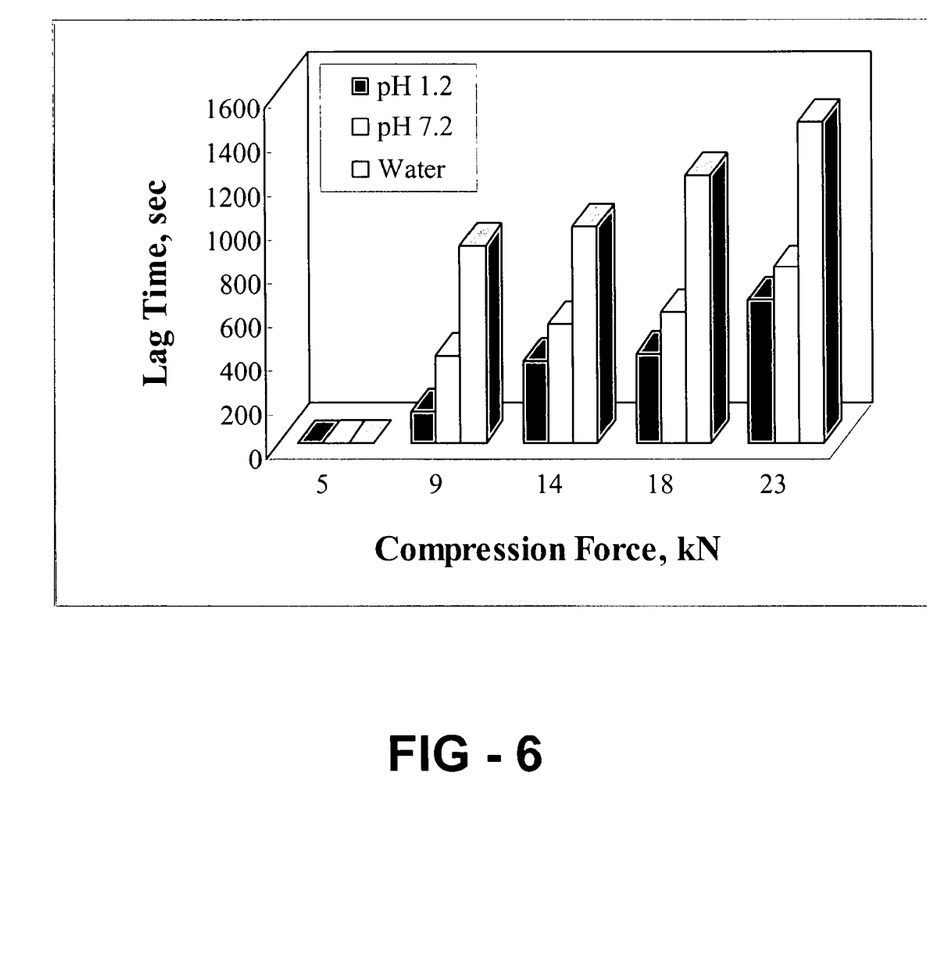
FIG. 6 is a graph illustrating lag time as a function of compression force for the gastroretentive composition of the present invention aloft water, a fluid having a pH of 1.2, and a fluid having a pH of 7.2.

The tablet of Example 6 is evaluated for lag time aloft water, the fluid having a pH of 1.2, and the fluid having a pH of 7.2 as a function of compression forces between 5 and 23 kN. As shown in FIG. 6, the tablet of Example 6 has a higher lag time aloft water than aloft fluid having a pH. The lag times are about 2 times lower aloft fluid having a pH than aloft water at all compression forces between 5 and 23 kN. Therefore, the gastroretentive composition of Example 6 exhibits improved lag time aloft a fluid having a pH of gastric fluids, i.e., from 1.2 to 7.2.

Example 9 and Comparative Example 10

A gastroretentive composition, Example 9, is formed by providing 340 mg of excipient component B in powder form and 200 mg of active ingredient component C in powder form. Excipient component B and active ingredient component C are combined in the blender for about 5 minutes at an ambient temperature of about 25° C., and powder sieved through the U.S.S. #20 mesh screen to form a fourth mixture in powder form. The fourth mixture is compressed on the Carver press to form a tablet, Example 9, comprising excipient component B and active ingredient component C. The tablet of Example 9 has a weight of 540 mg.

A 200 mg tablet of a commercially available conventional instant-release ibuprofen, Comparative Example 10, is provided.

Figure 5:
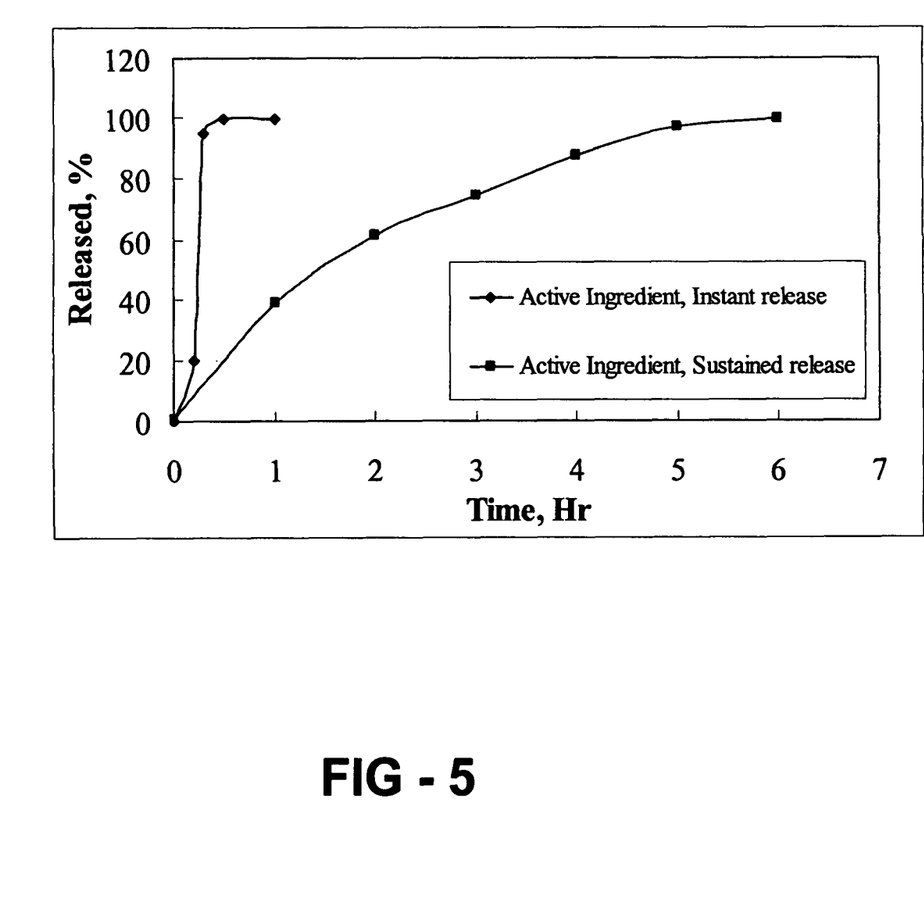
FIG. 5 is a graph illustrating percent of active ingredient component released as a function of time for the gastroretentive composition of the present invention as compared to a conventional composition.

Each of the tablets of Example 9 and Comparative Example 10 is evaluated for dissolution time in water at 25° C. As shown in FIG. 5, the tablets of Example 9 comprising PVA-PEG Copolymer+PVA release greater than 90% of the active ingredient component C and have a dissolution time of greater than 4 hours in water at 25° C. In contrast, as shown in FIG. 5, the conventional instant-release tablets of Comparative Example 10 release greater than 90% of the ibuprofen and have a dissolution time of 30 minutes in water at 25° C. Therefore, the tablets of Example 9 comprising PVA-PEG Copolymer+PVA provide improved extended- and/or sustained-release characteristics and excellent water solubility for gastroretentive compositions without the use of organic acids and inorganic bases in the gastroretentive compositions.

Examples 11-12

A gastroretentive composition, Example 11, is formed by providing 340 mg of excipient component B in powder form and 200 mg of active ingredient component D in powder form. Active ingredient component D is poorly-soluble carbamazepine commercially available from BASF Corporation of Florham Park, N.J. Excipient component B and active ingredient component D are combined in the blender for about 5 minutes at an ambient temperature of about 25° C., and powder sieved through the U.S.S. #20 mesh screen to form a fifth mixture in powder form. The fifth mixture is compressed on the Carver press to form a tablet, Example 11, comprising excipient component B and active ingredient component D. The tablet of Example 11 has a weight of 540 mg.

Likewise, a gastroretentive composition, Example 12, is formed by providing 340 mg of excipient component B in powder form and 200 mg of active ingredient component E in powder form. Active ingredient component E is water-soluble caffeine commercially available from BASF Corporation of Florham Park, N.J. Excipient component B and active ingredient component E are combined in the blender for about 5 minutes at an ambient temperature of about 25° C., and powder sieved through the U.S.S. #20 mesh screen to form a sixth mixture in powder form. The sixth mixture is compressed on the Carver press to form a tablet, Example 12, comprising excipient component B and active ingredient component E. The tablet of Example 12 has a weight of 540 mg.

Figure 7:
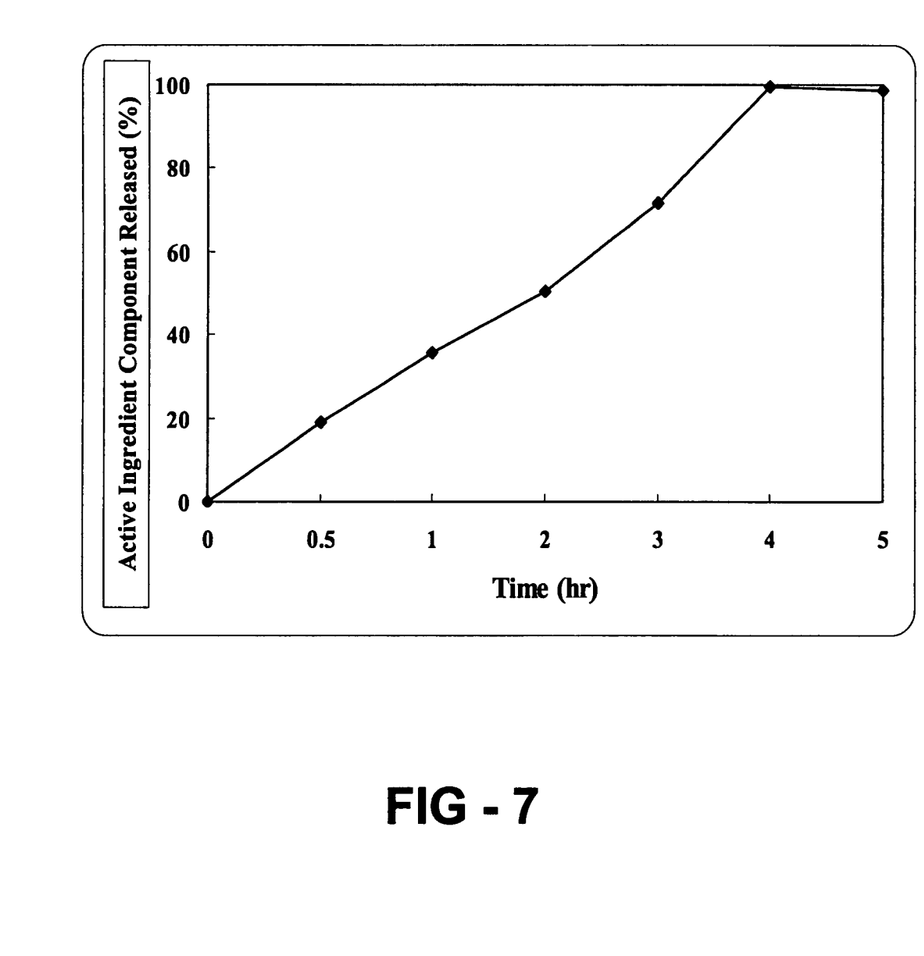
FIG. 7 is a graph illustrating percent of active ingredient component released as a function of time for the gastroretentive composition of the present invention comprising a poorly-soluble active ingredient component.
Figure 8:
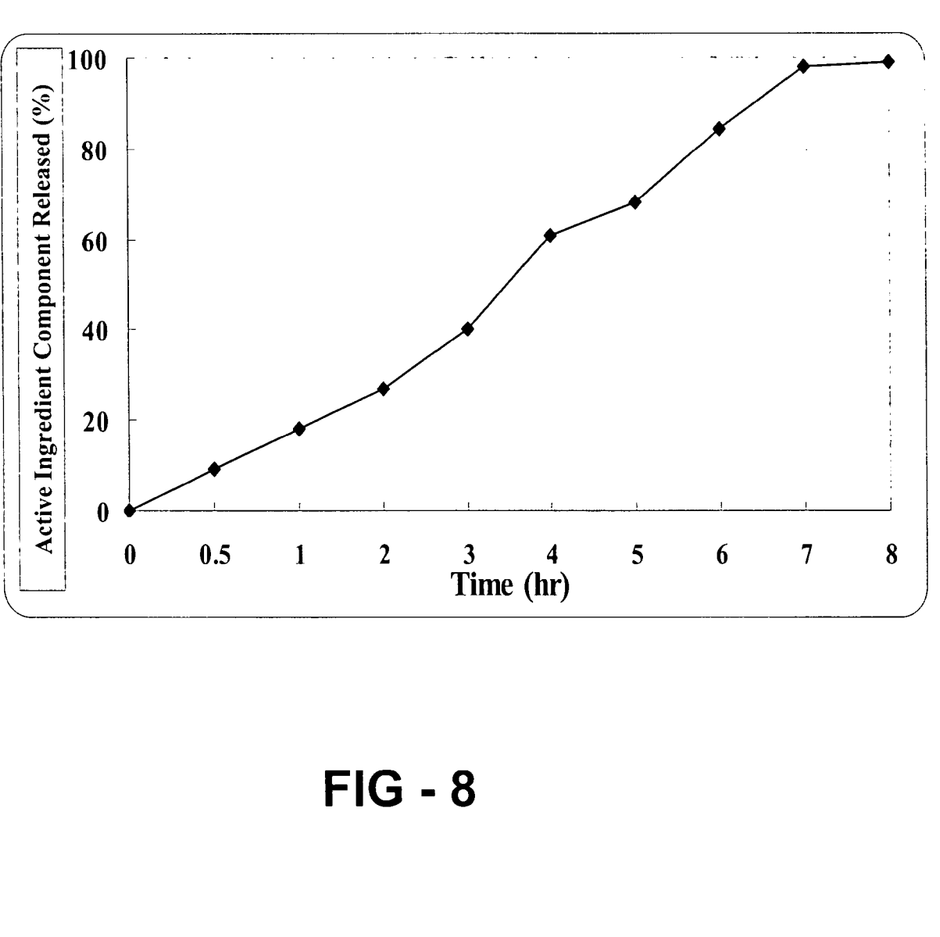
FIG. 8 is a graph illustrating percent of active ingredient component released as a function of time for the gastroretentive composition of the present invention comprising a water-soluble active ingredient component.

Each of the tablets of Examples 11-12 is evaluated for dissolution time in water at 25° C. As shown in FIG. 7, the tablet of Example 11 comprising PVA-PEG Copolymer+PVA (e.g. Kollicoat® Protect) releases greater than 95% of the active ingredient component D and has a dissolution time of 4 hours in water at 25° C. Similarly, as shown in FIG. 8, the tablet of Example 12 comprising PVA-PEG Copolymer+PVA (e.g. Kollicoat® Protect) releases greater than 95% of the active ingredient component E and has a dissolution time of 7 hours in water at 25° C. Therefore, the tablets of Examples 11-12 comprising PVA-PEG Copolymer+PVA provide improved extended- and/or sustained-release characteristics and excellent water solubility for gastroretentive compositions including an active ingredient component that is water-soluble or poorly-soluble without the use of organic acids and inorganic bases in the gastroretentive compositions.

The invention has been described in an illustrative manner, and it is to be understood that the terminology which has been used is intended to be in the nature of words of description rather than of limitation. Obviously, many modifications and variations of the present invention are possible in light of the above teachings. The invention may be practiced otherwise than as specifically described.

What is claimed is:
1. A gastroretentive composition comprising a mixture comprising:
    an active ingredient component; and
    an excipient component in powder form, said excipient component comprising;
        a first water-soluble reaction product produced from a precursor comprising a vinyl group; and
        a graft copolymer of polyethylene glycol and polyvinyl alcohol water-soluble reaction product produced from a precursor comprising a vinyl group wherein said first water-soluble reaction product and said second water-soluble reaction product may be the same or different,
    wherein said active ingredient component is present in said gastroretentive composition in an amount of from 5 to less than 50 parts by weight based on 100 parts by weight of said gastroretentive composition and wherein said gastroretentive composition is a floating drug delivery system, and wherein said active ingredient component is dispersed with said excipient component in said mixture.

2. A gastroretentive composition as set forth in claim 1 wherein said active ingredient component is in powder form.

3. A gastroretentive composition as set forth in claim 1 wherein said first water-soluble reaction product and said polyvinyl alcohol each independently have a weight average molecular weight of from 30,000 to 200,000 Daltons.

4. A gastroretentive composition as set forth in claim 1 wherein said first water-soluble reaction product is polyvinyl alcohol.

5. A gastroretentive composition as set forth in claim 1 wherein said first water-soluble reaction product is present in said excipient component in an amount of from 30 to 85 parts by weight based on 100 parts by weight of said excipient component.

6. A gastroretentive composition as set forth in claim 1 having a flotation time of from about 0 to 24 hours aloft fluid having a pH of from 1.2 to 7.2 at a temperature of about 37° C.

7. A gastroretentive composition as set forth in claim 6 having a lag time of from about 0 to 15 minutes aloft fluid having a pH of from 1.2 to 7.2 at a temperature of about 37° C.

8. A gastroretentive composition as set forth in claim 6 having a dissolution time of from about 0 to 24 hours in fluid having a pH of from 1.2 to 7.2 at a temperature of about 37° C.

9. A gastroretentive composition as set forth in claim 1 wherein said graft copolymer has a weight average molecular weight of from 40,000 to 50,000 Daltons.

10. A gastroretentive composition as set forth in claim 1 wherein said graft copolymer has a weight ratio of said polyvinyl alcohol to said polyethylene glycol of from 1:3 to 3:1.

11. A gastroretentive composition as set forth in claim 1 wherein said second polyvinyl alcohol is present in said copolymer in an amount of from 20 to 80 parts by weight based on 100 parts by weight of said copolymer.

12. A gastroretentive composition as set forth in claim 1 wherein said polyethylene glycol is present in said copolymer in an amount of from 5 to 30 parts by weight based on 100 parts by weight of said copolymer.

13. A gastroretentive composition as set forth in claim 1 further comprising an additive component selected from the group of an antiadherent, a colorant, a lubricant, a filler, a binder, a flavorant, a glidant, a preservative, a solubilizer, a disintegrant, and combinations thereof.

14. A gastroretentive composition as set forth in claim 1 further comprising a coating agent wherein said coating agent is a polymer.

15. A gastroretentive composition as set forth in claim 1 further comprising a granulating agent selected from the group of a polyvinyl pyrrolidone, polyvinyl acetate, polyvinyl alcohol, polyoxy propylene-polyoxy ethylene copolymer, a polyacrylic acid-based polymer, and combinations thereof.

16. A gastroretentive composition as set forth in claim 1 wherein said active ingredient component is an analgesic.

17. A gastroretentive composition comprising a mixture comprising:
an active ingredient component comprising ibuprofen; and
an excipient component in powder form, said excipient component comprising;
polyvinyl alcohol; and
a graft copolymer of polyethylene glycol and polyvinyl alcohol;
wherein said active ingredient component is dispersed with said excipient component in the mixture, wherein said active ingredient component is present in said gastroretentive composition in an amount of from 5 to less than 50 parts by weight based on 100 parts by weight of said gastroretentive composition and wherein said gastroretentive composition is a floating drug delivery system.

18. A method of forming a gastroretentive composition, said method comprising the steps of:
providing an active ingredient component in powder form;
providing an excipient component in powder form comprising;
a first water-soluble reaction product produced from a precursor comprising a vinyl group; and
a graft copolymer of polyethylene glycol and polyvinyl alcohol
mixing the active ingredient component and the excipient component to form a mixture in powder form;
aggregating the mixture to form an aggregation;
dry granulating the aggregation to form a plurality of granules; and
processing the plurality of granules to form the gastroretentive composition, wherein said active ingredient component is present in the gastroretentive composition in an amount of from 5 to less than 50 parts by weight based on 100 parts by weight of the gastroretentive composition and wherein the gastroretentive composition is a floating drug delivery system.

19. The method as set forth in claim 18 wherein said step of mixing comprises dispersing the active ingredient component with the excipient component in the mixture.

20. The method as set forth in claim 18 wherein the first water-solable reaction product is polyvinyl alcohol.

21. The method of forming a gastroretentive composition as set forth in claim 18 wherein the gastroretentive composition has a flotation time of from about 0 to 24 hours aloft fluid having a pH of from 1.2 to 7.2 at a temperature of about 37° C.

22. A gastroretentive composition as set forth in claim 1 wherein said active ingredient component is present in said gastroretentive composition in an amount of from 5 to 37 parts by weight based on 100 parts by weight of said gastroretentive composition.

23. A gastroretentive composition as set forth in claim 17 wherein said active ingredient component is present in said gastroretentive composition in an amount of from 5 to 37 parts by weight based on 100 parts by weight of said gastroretentive composition.

24. A gastroretentive composition as set forth in claim 1 wherein the mixture and the excipient component are not dissolved.

25. A gastroretentive composition as set forth in claim 17 wherein the mixture and the excipient component are not dissolved.

* * * * *

UNITED STATES PATENT AND TRADEMARK OFFICE
CERTIFICATE OF CORRECTION

PATENT NO. : 9,622,966 B2
APPLICATION NO. : 12/667793
DATED : April 18, 2017
INVENTOR(S) : Shaukat Ali et al.

Page 1 of 1

It is certified that error appears in the above-identified patent and that said Letters Patent is hereby corrected as shown below:

In the Claims

Claim 1, Column 16, Line 57, after "alcohol", delete "water-soluble reaction product produced from a precursor comprising a vinyl group wherein said first water-soluble reaction product and said second water-soluble reaction product may be the same or different,"

Claim 11, Column 17, Line 37, after "wherein said", delete "second"

Claim 20, Column 18, Line 41, delete "water-solable" and replace with -- water-soluble --

Signed and Sealed this
Third Day of October, 2017

Joseph Matal
*Performing the Functions and Duties of the
Under Secretary of Commerce for Intellectual Property and
Director of the United States Patent and Trademark Office*